United States Patent [19]

Meijer

[11] Patent Number: 4,837,287

[45] Date of Patent: Jun. 6, 1989

[54] T-ALKENYL PEROXY ESTERS AND THEIR USE AS INITIATORS AND CURING AGENTS

[75] Inventor: John Meijer, Deventer, Netherlands

[73] Assignee: Akzo N.V., Arnhem, Netherlands

[21] Appl. No.: 66,002

[22] Filed: Jun. 24, 1987

Related U.S. Application Data

[62] Division of Ser. No. 903,955, Sep. 4, 1986, Pat. No. 4,705,888.

[30] Foreign Application Priority Data

Sep. 30, 1985 [NL] Netherlands ............... 8502661

[51] Int. Cl.$^4$ ................................. C08F 4/32
[52] U.S. Cl. ......................... 526/231; 526/232; 526/232.5
[58] Field of Search ............. 526/232.5, 231, 232

[56] References Cited

U.S. PATENT DOCUMENTS

| | | | |
|---|---|---|---|
| 3,451,981 | 6/1969 | Rekers et al. | 526/232.5 |
| 3,451,989 | 6/1969 | Rekers et al. | 526/232.5 |
| 3,624,123 | 11/1971 | Lewis et al. | 526/232.5 |
| 3,687,867 | 8/1972 | Lewis et al. | 526/232.5 |
| 3,726,847 | 4/1973 | Lewis et al. | 560/302 |
| 3,781,255 | 12/1973 | Balwe et al. | 260/87.1 |
| 3,988,261 | 10/1976 | Barter et al. | 526/202 |
| 4,057,567 | 11/1977 | Friedman et al. | 560/302 |
| 4,079,074 | 3/1978 | Sanchez et al. | 560/302 |
| 4,219,675 | 8/1980 | Venkatram et al. | 568/563 |

FOREIGN PATENT DOCUMENTS 1181826 2/1970 United Kingdom .

OTHER PUBLICATIONS

Chemical Abstracts, vol. 69, p. 6218 (1968) 66704 p.
Chemical Abstracts, vol. 88, p. 574 (1978) 152262 s.

*Primary Examiner*—Joseph L. Schofer
*Assistant Examiner*—J. M. Reddick
*Attorney, Agent, or Firm*—Oliff & Berridge

[57] ABSTRACT

This disclosure relates to novel peroxy esters carrying a t-alkenyl, e.g. 2-methyl-3-buten-2-yl, peroxy group. These peroxy esters have shorter half-life periods of decomposition and are more reactive polymerization initiators and unsaturated polyester resin curing agents than the corresponding prior art peroxy esters carrying a t-alkyl, e.g. t-amyl, peroxy group.

4 Claims, No Drawings

T-ALKENYL PEROXY ESTERS AND THEIR USE AS INITIATORS AND CURING AGENTS

This is a division of application Ser. No. 903,955 filed Sept. 4, 1986 now U.S. Pat. No. 4,705,888.

BACKGROUND OF THE INVENTION

1. Field of the Invention

The invention relates to novel peroxy esters and to their use in the (co)-polymerization of ethylenically unsaturated compounds and in the curing of unsaturated polyester resins.

2. Description of Related Art

The use of t-alkyl peroxy esters as initiators and curing agents is generally known. Examples thereof are described in, int.al., U.S. Pat. Nos. 3,781,255, 4,057,567 and 4,219,675. On economical grounds, however, there is a continuous need for more efficient initiators and curing agents for the purpose of shortening the reaction times and increasing the production capacities. The invention has for its object to meet this need.

SUMMARY OF THE INVENTION

The peroxy ester according to the invention corresponds to the general formula:

$$R_1 \left( \begin{matrix} O & R_2 & R_4 & R_5 \\ \| & | & | & | \\ C-O-O-C-C=C \\ & | & & | \\ & R_3 & & R_6 \end{matrix} \right)_m \quad \text{I}$$

wherein $m=1$ or 2, and when $m=1$, $R_1$ has the meaning of
- a cyclohexyl group,
- a cyclohexenyl group,
- a phenyl group which is substituted or not with one or more chlorine aatoms or methyl groups,
- a group $$\begin{matrix} R_9 \\ | \\ R_8-C- \\ | \\ R_7 \end{matrix}$$

wherein $R_7$ and $R_8$ are the same or different and represent a hydrogen atom or an alkyl group containing 1-10 carbon atoms, and $R_9$ represents a hydrogen atom, an alkyl group containing 1-10 carbon atoms, an alkoxy group containing 1-6 carbon atoms, a phenyl group or a phenoxy group or
- a group $$\begin{matrix} R_{11} \\ | \\ R_{10}-CH=C- \end{matrix}$$

wherein $R_{10}$ and $R_{11}$ are the same or different and represent a hydrogen atom or an alkyl group containing 1-4 carbon atoms;

when
$m=2$, $R_1$ has the meaning of an alkylene group containing 1-11 carbon atoms,
- a cyclohexylene group,
- a phenylene group or
- a group of the formula $-CH_2-O-CH_2-$;

$R_2$ and $R_3$ are the same or different and represent an alkyl group containing 1-4 carbon atoms or together represent a pentamethylene bridge; and $R_4$, $R_5$ and $R_6$ are the same or different and represent a hydrogen atom or an alkyl group containing 1-4 carbon atoms.

DETAILED DESCRIPTION OF THE INVENTION

The above-indicated upper limits with regard to the numbers of carbon atoms for $R_1$ up to and including $R_{11}$ are governed by practical considerations. The alkyl groups and the alkylene group indicated may be linear or branched.

Essential to the peroxy esters according to the invention is the presence of the structural element $$\begin{matrix} R_2 & R_4 & R_5 \\ | & | & | \\ -O-O-C-C=C \\ | & & | \\ R_3 & & R_6 \end{matrix}$$

where the carbon atom linked to the peroxide bond should have a tertiary structure and the double bond is separated from the peroxide bond by this carbon atom.

It has been found that the t-alkenyl peroxy esters according to the invention have shorter half-life periods of decomposition and are more reactive initiators and curing agents than the prior art t-alkyl peroxy esters of otherwise the same structure.

The peroxy esters according to the invention may be divided into monoperoxy esters ($m=1$) and diperoxy diesters ($m=2$). They may be prepared in the usual manner by reacting an acid chloride with a t-alkenyl hydroperoxide in the presence of a base.

The acid chlorides suitable for this purpose are prepared by reacting a carboxylic acid with a chlorinating reagent, such as $PCl_3$, $POCl_3$, $PCl_5$, $COCl_2$ and $SOCl_2$. The carboxylic acid used has the general structural formula:

$$R_1 \left( \begin{matrix} O \\ \| \\ C-OH \end{matrix} \right)_m$$

wherein $R_1$ and m have the above-indicated meaning.

As examples of suitable monocarboxylic acids may be mentioned cyclohexanecarboxylic acid, 2-cyclohexene-1-carboxylic acid, benzoic acid, o-, m- and p-methylbenzoic acid, o-chlorobenzoic acid, 2,4-dichlorobenzoic acid, acetic acid, n-heptanoic acid, lauric acid, 2-ethylhexanoic acid, 3,5,5-trimethylhexanoic acid, phenylacetic acid, isobutyric acid, 2-methylbutyric acid, 2-ethylbutyric acid, 2-phenylbutyric acid, 2-methylpentanoic acid, 2,2-dimethyloctanoic acid, pivalic acid, neohexanoic acid, neoheptanoic acid, neooctanoic acid, neononanoic acid, neodecanoic acid, neotridecanoic acid (the last five neo acids having such a structure that not more than one of the groups $R_7$, $R_8$ and $R_9$ is a methyl group, as described in U.S. Pat. No. 3,624,123), methoxyacetic acid, ethoxyacetic acid, phenoxyacetic acid, acrylic acid, methacrylic acid, crotonic acid and 2-methylcrotonic acid (of the last four acids methacrylic acid, crotonic acid and 2-methylcrotonic acid are preferred).

As examples of suitable dicarboxylic acids may be mentioned malonic acid, succinic acid, glutaric acid, 2,2-dimethyl-1,5-pentanedioic acid, adipic acid, azelaic acid, 1,10-decanedicarboxylic acid, 1,11-undecanedicarboxylic acid, 1,4-cyclohexanedicarboxylic acid, 1,2-cyclohexanedicarboxylic acid, phthalic acid, isophthalic acid, terephthalic acid and diglycolic acid. The t-alkenyl hydroperoxides suitable for the preparation of the present peroxy esters satisfy the general structural formula:

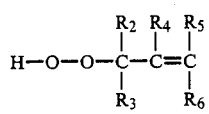

wherein $R_2$ through $R_6$ have the above-indicated meaning. They are prepared in the usual manner by reacting a t-alkenyl alcohol with hydrogen peroxide in the presence of a strongly acid catalyst such as sulphuric acid.

As examples of t-alkenyl hydroperoxides suitable to be used in the preparation of the present peroxyesters may be mentioned:
2-methyl-3-buten-2-yl hydroperoxide,
3-methyl-1-penten-3-yl hydroperoxide,
3,4-dimethyl-1-penten-3-yl hydroperoxide,
3-ethyl-1-penten-3-yl hydroperoxide,
3isopropyl-4-methyl-1-penten-3-yl hydroperoxide,
3-methyl-1-hexen-3-yl hydroperoxide,
3-n-propyl-1-hexen-3-yl hydroperoxide,
1-vinylcyclohexyl-1-yl hydroperoxide,
2-methyl-3-penten-2-yl hydroperoxide, and
2,3,4-trimethyl-3-penten-2-yl hydroperoxide.

As the starting alcohol is satisfactorily available, it is preferred that use should be made of 2-methyl-3-buten-2-yl hydroperoxide (where $R_2$ and $R_3$ represent methyl groups and $R_4$, $R_5$ and $R_6$ hydrogen atoms).

All the peroxy esters according to the invention satisfy the above-described formula I. Preferred are those peroxy esters where in formula I when $m=1$, $R_1$ has the meaning of
a cyclohexyl group,
a phenyl group,
an o-chlorophenyl group,
an o-methylphenyl group,
a group

wherein $R_7$ and $R_8$ are the same or different and represent a hydrogen atom or an alkyl group containing 1–10 carbon atoms and $R_9$ represents a hydrogen atom, an alkyl group containing 1–10 carbon atoms, a phenyl group or a phenoxy group or a group

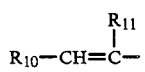

wherein $R_{10}$ and $R_{11}$ are the same or different and represent a hydrogen atom or a methyl group; when $m=2$, $R_1$ has the meaning of an alkylene group containing 3–11 carbon atoms, more particularly 3–8 carbon atoms,
a 1,4-cyclohexylene group,
an o-, m- or p-phenylene group or
a group of the formula $-CH_2-O-CH_2-$.

Typical examples of suitable peroxyesters according to the invention are
2-methyl-3-buten-2-yl peroxycyclohexanecarboxylate,
2-methyl-3-buten-2-yl peroxy-2-cyclohexene-1-carboxylate,
2-methyl-3-buten-2-yl peroxybenzoate,
2-methyl-3-buten-2-yl peroxy-o-methylbenzoate,
2-methyl-3-buten-2-yl peroxy-o-chlorobenzoate,
2-methyl-3-buten-2-yl peroxyacetate.
2-methyl-3-buten-2-yl peroxyisobutyrate,
2-methyl-3-buten-2-yl peroxypivalate,
2-methyl-3-buten-2-yl peroxyneohexanoate,
2-methyl-3-buten-2-yl peroxyneoheptanoate,
2-methyl-3-buten-2-yl peroxyneooctanoate,
2-methyl-3-buten-2-yl peroxyneononanoate,
2-methyl-3-buten-2-yl peroxyneodecanoate,
2-methyl-3-buten-2-yl peroxyneotridecanoate,
2-methyl-3-buten-2-yl peroxy-2-methylbutyrate,
2-methyl-3-buten-2-yl peroxy-2-ethylbutyrate,
2-methyl-3-buten-2-yl peroxy-2-methylpentanoate,
2-methyl-3-buten-2-yl peroxy-2-ethylhexanoate,
2-methyl-3-buten-2-yl peroxy-3,5,5-trimethylhexanoate,
2-methyl-3-buten-2-yl peroxyphenylacetate,
2-methyl-3-buten-2-yl peroxy-2-phenylbutyrate,
2-methyl-3-buten-2-yl peroxylauroate,
2-methyl-3-buten-2-yl peroxyphenoxyacetate,
2-methyl-3-buten-2-yl peroxyacrylate,
di(2-methyl-3-buten-2-yl) diperoxyglutarate,
di(2-methyl-3-yl) diperoxyadipate,
di(2-methyl-3-buten-2-yl) diperoxyazelate,
di(2-methyl-3-buten-2-yl) diperoxysebacate,
di(2-methyl-3-buten-2-yl) diperoxy-1,10-decanedicarboxylate,
di(2-methyl-3-buten-2-yl) diperoxy-1,11-undecanedicarboxylate,
di(2-methyl-3-buten-2-yl) diperoxy-1,4-cyclohexanedicarboxylate,
di(2-methyl-3-buten-2-yl) diperoxyphthalate,
di(2-methyl-3-buten-2-yl) diperoxyisophthalate,
di(2-methyl-3-buten-2-yl) diperoxyterephthalate,
di(2-methyl-3-buten-2-yl) diperoxydiglycolate.

The peroxy ester according to the invention is very suitable to be used in the polymerization or copolymerization of ethylenically unsaturated compounds. As examples of ethylenically unsaturated compounds may be mentioned olefins, such as ethylene, styrene, α-methylstyrene and chlorostyrene; diolefins, such as 1,3-butadiene and isoprene; vinyl esters, such as vinyl acetate and vinyl propionate; unsaturated nitriles, such as acrylonitrile and methacrylonitrile; acrylic acid, methacrylic acid and their esters and amides; vinyl halo and vinylidene halo compounds, such as vinyl chloride, vinyl bromide, vinyl fluoride, vinylidene chloride and vinylidene fluoride; perhalo olefins, such as tetrafluoroethylene; vinyl ethers, such as methyl vinyl ether and n-butyl vinyl ether; and mixtures thereof. It is preferred that the present peroxy ester should be used in the polymerization of vinyl chloride, styrene, ethylene or methyl methacrylate, more particularly in the suspension, emulsion or mass polymerization of vinyl chloride.

The present peroxy esters may be used as such or in combination with other initiators. This last-mentioned embodiment is used to obtain a most constant reaction speed throughout the polymerization process. To this end use is made of a combination of a relatively rapid and a relatively slow initiator. As examples of combinations commonly used in actual practice may be mentioned acetylcyclohexane sulphonyl peroxide with dilauroyl peroxide and 2,4,4-trimethylpentane-2-yl peroxyphenoxy acetate with bis(4-t-butylcyclohexyl)peroxydicarbonate. It has been found that upon replacement in these combinations of, respectively, acetylcyclohexane sulphonyl peroxide and 2,4,4-trimethylpentane-2-yl peroxyphenoxy acetate with the present peroxy esters, the resulting initiator combinations lead to satisfactory results in the polymerization of vinyl chloride.

The present peroxy ester is to be used in an amount of 0.005 to 3% by weight, preferably 0.01 to 0.5% by weight, and in particular 0.02 to 0.2% by weight, calculated on the weight of the monomer. The temperature to be used is in the range of 20° C. to 250° C., preferably 30° C. to 200° C.

The peroxy ester according to the invention is also suitable to be applied in the curing of unsaturated polyester resins. Such resins generally comprise an unsaturated polyester, a polymerizable monomer, and, optionally, fillers. An example of an unsaturated polyester resin is one of which the polyester component consists of the esterification product of 1,2-propylene glycol and maleic anhydride and phthalic anhydride and of which the polymerizable monomer is styrene. The amount of peroxy ester to be used is 0.05 to 5% by weight, preferably 0.5 to 2% by weight, calculated on the weight of the unsaturated polyester resin. The temperature to be used is in the range of about 20° C. to 200° C.

For the above-mentioned uses also combinations of the present peroxy esters may be employed.

The peroxy esters according to the invention may be prepared, transported, stored and applied as such or formulated as solutions, aqueous suspensions or emulsions, pastes, etc. Which of these alternatives is to be preferred depends, int.al., on safety considerations (desensitizing) and considerations regarding the nature of their use (the aqueousness or not of the polymerization system, feeding the peroxy esters into closed reaction systems, etc.).

As suitable desensitizing agents may be mentioned the paraffinic hydrocarbons commonly employed for this purpose, such as isododecane and white spirit, plasticizers, such as esters of phthalic acid, solid carrier materials, such as silica, water, etc. For the formulation of aqueous suspensions (in the case of solid peroxy esters) or emulsions (in the case of liquid peroxy esters) use may be made of the emulsifiers and/or thickening agents commonly employed to this end. Examples of such emulsifiers and thickening agents are described in U.S. Patent Specification No. 3,988,261. If for safety reasons said suspensions and emulsions are to be transported and stored at low temperature, then there may optionally be added to them anti-freeze agents, such as methanol, ethanol, propanol, isopropanol and butanol.

The following examples serve to illustrate the invention.

EXAMPLE I

Preparation of 2-methyl-3-buten-2-yl hydroperoxide

To a stirred mixture cooled at 5° C. of 9.7 g of 70%-hydrogen peroxide (0.20 moles) and 0.9 g of 85%-sulphuric acid (0.008 moles) there were added dropwise over a period of 5 minutes 8.6 g of 2-methyl-3-buten-2-ol (0.10 moles), care being taken that the temperature of the reaction mixture remained between 5° and 10° C. Subsequently, the mixture was stirred for 20 minutes at 10° C., and then for 60 minutes at 20° C. Next, 6 g of solid sodium sulphate were added to the reaction mixture. After the organic layer had been isolated, it was washed three times with a saturated aqueous solution of sodium sulphate. Finally, the organic layer was dried with MgSO$_4$. After filtration 9.2 g of product were obtained as colourless liquid. Its active oxygen content was 13.56%, which corresponds to a yield of 78%. The identity of the product was confirmed by NMR and IR spectroscopy.

EXAMPLE 2

Preparation of 2-methyl-3-buten-2-yl peroxypivalate

To a stirred mixture cooled at 10° C. of 10 g of demineralized water, 17.3 g of a 45% by weight-potassium hydroxide solution in water (0.139 moles) and 12.9 g of 2-methyl-3-buten-2-yl hydroperoxide (0.120 moles) there were added over a period of 25 minutes 14.5 g of pivaloyl chloride (0.120 moles); the temperature of the reaction mixture was kept at 10°-12° C. Stirring was continued for 1 hour, after which the organic layer was isolated. It was washed successively with an aqueous solution of 10% by weight-KOH (15 min, 10° C.), an aqueous bisulphite/acetate buffer (20 min., 10° C.) and a dilute solution of sodium bicarbonate in water (2x). Finally, the organic layer was dried with MgSO$_4$ and the product was isolated by filtration. There were obtained 17.3 g of colourless oil containing 97.7% of peroxy ester, which corresponds to a yield of 75.6%. The identity of the product was confirmed by IR and NMR spectroscopy ($^1$H and $^{13}$C).

EXAMPLE 3

Preparation of other 2-methyl-3-buten-2-yl peroxy esters

Use being made of the same procedure as described in Example 2, except that the pivaloyl chloride was replaced with the appropriate acid chlorides in the appropriate amounts, the following peroxy esters were prepared. All products obtained were colourless oils.

2-methyl-3-buten-2-yl peroxyneodecanoate
assay: 95% yield: 72.9%

2-methyl-3-buten-2-yl peroxyneohexanoate
assaay: 93.8% yield: 79.6%

2-methyl-3-buten-2-yl peroxy-2-ethylhexanoate
assay: 98.3% yield: 88.8%

2-methyl-3-buten-2-yl peroxybenzoate
assay: 98.8% yield: 85.2%

2-methyl-3-buten-2-yl peroxyphenylacetate
assay: 95.1% yield: 72.7%

2-methyl-3-buten-2-yl peroxy-2-methylpropanoate
assay: 96.8% yield: 80% di(2-methyl-3-buten-2-yl) diperoxyazelate
assay: 95.4% yield: 57.3% di(2-methyl-3-buten-2-yl) diperoxydiglycolate
assay: 94.2% yield: 70.1%

Of all products the identity was confirmed by IR and NMR spectroscopy.

EXAMPLE 4

Decomposition tests were conducted in chlorobenzene as solvent (concentration: 1 mole/liter). Of the peroxy esters prepared in Example 2 and 3 the temperatures are given in Table 1 at which the half life periods of decomposition are 10 hours ($t_{\frac{1}{2}10}$), 1 hour ($t_{\frac{1}{2}1}$) and 0.1 hour ($t_{\frac{1}{2}0.1}$). For comparison the Table also gives the temperatures for $t_{\frac{1}{2}10}$, $t_{\frac{1}{2}1}$, and $t_{\frac{1}{2}0.1}$ of esters which are derived from the same carboxylic acids but carry the prior art t-amyl (=2-methylbutane-2-yl) peroxy group. The results show that the 2-methyl-3-butene-2-yl peroxy esters according to the invention display a higher rate of decomposition than the corresponding t-amyl peroxy esters which are of nearly identical structure but are outside the scope of the invention.

TABLE 1

| Peroxyester | $t_{\frac{1}{2}10}$ (°C.) | $t_{\frac{1}{2}1}$ (°C.) | $t_{\frac{1}{2}0.1}$ (°C.) |
| --- | --- | --- | --- |
| 2-methyl-3-butene-2-yl peroxypivalate | 44.2 | 63.5 | 85.3 |
| t-amyl peroxypivalate | 50.0 | 69.0 | 91.0 |
| 2-methyl-3-buten-2-yl peroxyneodecanoate | 38.1 | 56.6 | 77.5 |
| t-amyl peroxyneodecanoate | 39.0 | 59.0 | 83.0 |
| 2-methyl-3-buten-2-yl peroxyneohexanoate | 42.0 | 61.2 | 83.0 |
| t-amyl peroxyneohexanoate | 46.09 | 66.5 | 88.7 |
| 2-methyl-3-buten-2-yl peroxy-2-ethyl-hexanoate | 58.1 | 81.2 | 105.0 |
| t-amyl peroxy-2-ethylhexanoate | 59.0 | 82.4 | 109.2 |
| 2-methyl-3-buten-2-yl peroxybenzoate | 84.6 | 104.3 | 126.4 |
| t-amyl peroxybenzoate | 95.5 | 116.0 | 138.9 |
| 2-methyl-3-buten-2-yl peroxyphenylacetate | 57.1 | 77.1 | 99.6 |
| t-amyl peroxyphenylacetate | 62.0 | 82.3 | 105.4 |
| 2-methyl-3-buten-2-yl peroxy-2-methyl-propanoate | 75.0 | 97.2 | 122.4 |
| t-amyl peroxy-2-methylpropanoate | 93.0 | 111.6 | 132.2 |
| di(2-methyl-3-buten-2-yl) diperoxyazelate | 87.0 | 108.3 | 132.1 |
| di-t-amyl diperoxyazelate | 94.0 | 114.2 | 136.8 |
| di(2-methyl-3-buten-2-yl) diperoxydiglycolate | 26.4 | 45.1 | 66.1 |
| di-t-amyl diperoxydiglycolate | 36.0 | 53.9 | 73.9 |

EXAMPLE 5

In this Example the results obtained with peroxy esters according to the invention used as initiators in the polymerization of vinyl chloride are compared with those obtained with the corresponding t-amyl peroxy esters which are of nearly identical structure but are outside the scope of the invention.

The following general procedure was used.

To a solution in 340 g of water of 0.2 g of polyvinyl alcohol (Gohsenol KP-08, a commercial product of Nippon Gohsei) and 0.84 g of sodium bicarbonate contained in an autoclave (1-liter) there were added, under an atmosphere of nitrogen, 200 g of vinyl chloride and the initiator. The stirring speed was 750 r.p.m. The reaction mixture was heated and after a certain reaction time (including the heating time) the reaction mixture was cooled and unreacted vinyl chloride removed, after which polyvinyl chloride was isolated by filtration. The product was washed and finally dried for 16 hours at 50° C. From the weight of the resulting polymer the conversion was calculated.

The process data as regards type of peroxy ester, amount of peroxy ester (calculated as pure peroxy ester), reaction temperature and reaction time are summarized in Table 2. Also summarized in Table 2 are the conversions of vinyl chloride obtained. Judged by their higher conversion rates the peroxy esters according to the invention are clearly more active initiators than the corresponding t-amyl peroxy esters.

TABLE 2

| Peroxy ester | Amount (g) | Temp. (°C.) | Conversion (%) after a reaction time of | | |
| --- | --- | --- | --- | --- | --- |
| | | | 3 hrs | 5 hrs | 7 hrs |
| peroxyneodecanoate | | | | | |
| 2-methyl-3-buten-2-yl | 0.24 | 40 | 40 | 62 | 85 |
| t-amyl peroxyneodecanoate | 0.24 | 40 | 23 | 40 | 58 |
| 2-methyl-3-buten-2-yl | 0.04* | 55 | 75 | 92 | — |
| t-amyl peroxypivalate | 0.04* | 55 | 65 | 90 | — |
| 2-methyl-3-buten-2-yl | 0.11 | 55 | 37 | 74 | 92 |
| t-amyl peroxy-2-ethylhexanoate | 0.11 | 55 | 30 | 66 | 91 |
| 2-methyl-3-buten-2-yl | 0.23 | 60 | 25 | 54 | 87 |
| t-amyl diperoxy-1,4-cyclo-hexanedicarboxylate | 0.23 | 60 | 20 | 45 | 81 |
| di(2-methyl-3-buten-2-yl) | 0.34 | 70 | 60 | 85 | — |
| di-t-amyl | 0.34 | 70 | 38 | 65 | — |

*In addition 0.1 g of bis(4-t-butylcyclohexyl)peroxydicarbonate was used.

EXAMPLE 6

In this Example the results obtained with peroxy esters according to the invention used as initiators in the polymerization of methyl methacrylate are compared with those obtained with the corresponding t-amyl peroxy esters which are of nearly identical structure but are outside the scope of the invention.

The following general procedure was used.

Into each of three 4-ml ampules which all contained a mixture of 0.97 g of methyl methacrylate and 0.53 g of toluene the initiator was introduced under a nitrogen atmosphere. After respectively 2, 4 and 6 hours' reaction time at elevated temperature the reaction was stopped by mixing the contents of an ampule with 20 g of dichloromethane containing 0.048 g of 2,6-di-t-butyl-4-methylphenol. Subsequently, the degree of conversion was determined by gaschromatographic analysis, use being made of benzene as internal standard. The process data as regards type of peroxy ester, amount of peroxyester (calculated as pure peroxy ester) and reaction temperature are summarized in Table 3. Also summarized in the Table are the conversions of methyl methacrylate obtained. As clearly shown by their higher conversion rates the peroxy esters of the invention are more active initiators than the corresponding t-amyl peroxy esters.

TABLE 3

| Peroxy ester | Amount (mg) | Temp. (°C.) | Conversion (%) after | | |
|---|---|---|---|---|---|
| | | | 2 hrs | 4 hrs | 6 hrs |
| peroxypivalate | | | | | |
| 2-methyl-3-butene-2-yl | 2.10 | 60 | 38.1 | 68.2 | 96.8 |
| t-amyl | 2.10 | 60 | 32.9 | 56.7 | 93.3 |
| peroxyneohexanoate | | | | | |
| 2-methyl-3-butene-2-yl | 1.89 | 60 | 36.8 | 66.5 | 95.6 |
| t-amyl | 1.89 | 60 | 36.0 | 58.8 | 94.7 |
| peroxy-2-ethylhexanoate | | | | | |
| 2-methyl-3-butene-2-yl | 2.35 | 70 | 28.3 | 53.3 | 97.2 |
| t-amyl | 2.35 | 70 | 28.0 | 41.6 | 92.6 |
| peroxyphenylacetate | | | | | |
| 2-methyl-3-butene-2-yl | 2.28 | 70 | 53.5 | 86.3 | 99.1 |
| t-amyl | 2.28 | 70 | 48.5 | 76.6 | 98.2 |

EXAMPLE 7

Into each of two 4-ml ampules styrene was mass polymerized at 110° C. using an initiator according to the invention, viz. 2-methyl-3-buten-2-yl peroxybenzoate, in an amount of 0.375 mmoles (calculated as pure peroxy ester) per 100 g of styrene in the one experiment and di(2-methyl-3-buten-2-yl) diperoxyazelate in an amount of 0.40 mmoles (calculated as pure diperoxy diester) per 100 g of styrene in the other. In both experiments a conversion of more than 99%, as determined by gaschromatographic analysis, was obtained after 8 hours' reaction time.

EXAMPLE 8

In this Example the results obtained with peroxy esters according to the invention used as curing agents for unsaturated polyester resins are compared with those obtained with t-amyl peroxy esters which are of nearly identical structure but are outside the scope of the invention, use being made of the procedures outlined in SPI Handbook of Reinforced Plastics, published by the Reinhold Publishing Corp., New York, pp. 36-37 (1964).

The unsaturated polyester resin used was a mixture of an unsaturated polyester and styrene monomer. The unsaturated polyester was an alkyd resin prepared by esterifying (to an Acid No. of about 50) the following components: maleic anhydride (1 mole), phthalic anhydride (1 mole), ethylene glycol (1.1 mole) and propylene glycol (1.1 mole). To the resulting resin were added 100 ppm of hydroquinone inhibitor, after which 65 parts of this resin were diluted with 35 parts of styrene.

To 25 g of the above-described unsaturated polyester resin were added 250 mg of peroxy ester (calculated as pure peroxy ester); subsequently, the time-temperature characteristics were determined in accordance with SPI, use being made of various bath temperatures.

The results are summarized in Table 4. They show that in the curing of unsaturated polyester resin the peroxy esters according to the invention are more active than the corresponding t-amyl peroxy esters.

In Table 4 the following abbreviations are used:
gt = gel time
mct = minimum cure time
ttp = time to peak
pe = peak exotherm

TABLE 4

| | t-amyl | | | 2-methyl-3-buten-2-yl | | |
|---|---|---|---|---|---|---|
| peroxyneo hexanoate | | | | | | |
| bath temp. (°C.) | 40 | 50 | 60 | 30 | 40 | 60 |
| gt (min) | | 27.2 | 8.0 | | 35.8 | 3.6 |
| mct (min) | | 29.1 | 9.7 | | 38.8 | 4.5 |
| ttp (min) | >60 | 32.9 | 16.7 | >60 | 39.4 | 8.6 |
| pe (°C.) | | 201 | 222 | | 195 | 219 |
| peroxypivalate | | | | | | |
| bath temp. (°C.) | 40 | 50 | 60 | 40 | 50 | 60 |
| gt (min) | | 35.6 | 8.7 | | 18.2 | 4.3 |
| mct (min) | | 37.7 | 9.9 | | 20.0 | 5.1 |
| ttp (min) | >60 | 40.9 | 15.5 | >60 | 23.9 | 10.6 |
| pe (°C.) | | 198 | 226 | | 207 | 230 |
| peroxy-2-ethyl-hexanoate | | | | | | |
| bath temp. (°C.) | 60 | 70 | 80 | 60 | 80 | |
| gt (min) | | 13.3 | 4.0 | 21.7 | 2.8 | |
| mct (min) | | 15.3 | 5.2 | 37.3 | 3.7 | |
| ttp (min) | >60 | 20.0 | 9.5 | 41.4 | 7.4 | |
| pe (°C.) | | 221 | 237 | 207 | 241 | |
| peroxy-2-methyl-propanoate | | | | | | |
| bath temp. (°C.) | 60 | 70 | 90 | 60 | 70 | |
| gt (min) | | 17.5 | 2.4 | 50.9 | 12.2 | |
| mct (min) | | 19.8 | 3.5 | 52.6 | 14.2 | |
| ttp (min) | >60 | 24.5 | 6.5 | 57.2 | 18.9 | |
| pe (°C.) | | 223 | 251 | 209 | 227 | |

We claim:

1. A (co)polymerization process, comprising (co)polymerizing an ethylenically unsaturated compound selected from the group consisting of vinyl chloride, ethylene, styrene and methyl methacrylate in the presence of a peroxy ester of the formula:

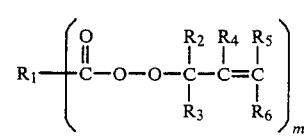

wherein m = 1 or 2, and when m = 1, $R_1$ is selected from the group consisting of a cyclohexyl group,
a cyclohexenyl group,
an unsubstituted phenyl group,
a phenyl group which is substituted with at least one substituent selected from the group consisting of chlorine atoms, methyl groups and mixtures thereof
a group

wherein $R_7$ and $R_8$ are independently selected from the group consisting of a hydrogen atom and an alkyl group containing 1–10 carbon atoms, and $R_9$ is selected from the group consisting of a hydrogen atom, an alkyl group containing 1–10 carbon atoms, an alkoxy group containing 1–6 carbon atoms, a phenyl group, a phenoxy group and a group

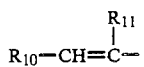

wherein $R_{10}$ and $R_{11}$ are independently selected from the group consisting of a hydrogen atom and an alkyl group containing 1-4 carbon atoms;

when m=2, $R_1$ is selected from the group consisting of
an alkylene group containing 1-11 carbon atoms,
a cyclohexylene group,
a phenylene group and
a group of the formula $-CH_2-O-CH_2-$;

$R_2$ and $R_3$ are either independently selected from the group consisting of an alkyl group containing 1-4 carbon atoms or together form a pentamethylene bridge; and $R_4$, $R_5$ and $R_6$ are independently selected from the group consisting of a hydrogen atom and an alkyl group containing 1-4 carbon atoms.

2. A process according to claim 1, wherein $R_2$ and $R_3$ represent methyl groups and $R_4$, $R_5$ and $R_6$ represent hydrogen atoms.

3. A process according to claim 2, wherein when m=1, $R_1$ is selected from the group consisting of
a cyclohexyl group,
a phenyl group,
an o-chlorophenyl group,
an o-methylphenyl group,
a group

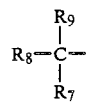

wherein $R_7$ and $R_8$ are independently selected from the group consisting of a hydrogen atom and an alkyl group containing 1-20 carbon atoms and $R_9$ is selected from the group consisting of a hydrogen atom, an alkyl group containing 1-10 carbon atoms, a phenyl group, a phenoxy group and
a group

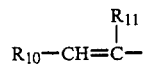

wherein $R_{10}$ and $R_{11}$ are independently selected from the group consisting of a hydrogen atom and a methyl group;

when m=2,
$R_1$ is selected from the group consisting of an alkylene group containing 3-11 carbon atoms,
a 1,4-cyclohexylene group,
an o-, m- or p-phenylene group, and
a group of the formula $-CH_2-O-CH_2-$.

4. A process according to claim 1, wherein said peroxy ester is selected from the group consisting of
2-methyl-3-buten-2-yl peroxypivalate,
2-methyl-3-buten-2-yl peroxy-2-ethylhexanoate,
2-methyl-3-buten-2-yl peroxyneodecanoate,
2-methyl-3-buten-2-yl peroxyneohexanoate,
2-methyl-3-buten-2-yl peroxybenzoate,
2-methyl-3-buten-2-yl peroxy-2-methylpropanoate,
2-methyl-3-buten-2-yl peroxyphenylacetate,
2-methyl-3-buten-2-yl peroxy-3,5,5-trimethylhexanoate
di(2-methyl-3-buten-2-yl)diperoxy-1,4-cyclohexanedicarboxylate,
di(2-methyl-3-buten-2-yl)diperoxyazelate and
di(2-methyl-3-buten-2-yl)diperoxydiglycolate.

* * * * *

UNITED STATES PATENT AND TRADEMARK OFFICE
CERTIFICATE OF CORRECTION

PATENT NO. : 4,837,287
DATED : June 6, 1989
INVENTOR(S) : John MEIJER

It is certified that error appears in the above-identified patent and that said Letters Patent is hereby corrected as shown below:

Column 1, line 40, change "aatoms" to --atoms--.

Column 3, line 29, change "3isopropyl" to --3-isopropyl--.

Column 7, line 15, change "butene-" to --buten---;
        line 20, change "46.09" to --46.9--.

Column 9, lines 9, 12, 15 and 18, change "butene-" to --buten---.

Signed and Sealed this

Fourth Day of September, 1990

*Attest:*

HARRY F. MANBECK, JR.

*Attesting Officer*     *Commissioner of Patents and Trademarks*